(12) United States Patent
Hosoi et al.

(10) Patent No.: US 8,975,021 B2
(45) Date of Patent: Mar. 10, 2015

(54) METHOD FOR DETECTING RHABDOMYOSARCOMA USING SAMPLE DERIVED FROM BODY FLUID

(75) Inventors: Hajime Hosoi, Kyoto (JP); Mitsuru Miyachi, Kyoto (JP)

(73) Assignees: Kyoto Prefectural Public University Corporation, Kyoto-Shi (JP); LSIP, LLC, Tokyo (JP)

( * ) Notice: Subject to any disclaimer, the term of this patent is extended or adjusted under 35 U.S.C. 154(b) by 66 days.

(21) Appl. No.: 13/639,183

(22) PCT Filed: Apr. 7, 2011

(86) PCT No.: PCT/JP2011/058843
§ 371 (c)(1),
(2), (4) Date: Feb. 19, 2013

(87) PCT Pub. No.: WO2011/126089
PCT Pub. Date: Oct. 13, 2011

(65) Prior Publication Data
US 2013/0203062 A1 Aug. 8, 2013

(30) Foreign Application Priority Data
Apr. 8, 2010 (JP) ................................ 2010-089180

(51) Int. Cl.
*C12Q 1/68* (2006.01)
(52) U.S. Cl.
CPC ........ *C12Q 1/6886* (2013.01); *C12Q 2600/178* (2013.01); *C12Q 2600/158* (2013.01)
USPC .......................................... 435/6.1; 435/6.12

(58) Field of Classification Search
None
See application file for complete search history.

(56) References Cited

U.S. PATENT DOCUMENTS

2012/0059159 A1* 3/2012 Ponzetto et al. ............. 536/24.5

FOREIGN PATENT DOCUMENTS

| WO | WO-2008/117278 A2 | 10/2008 |
| WO | WO-2008/117278 A3 | 10/2008 |

OTHER PUBLICATIONS

Taulli et al. (The muscle-specific microRNA miR-206 blocks human rhabdomyosarcoma growth in xenotransplanted mice by promoting myogenic differentiation, J. Clin. Invest. 119:2366-2378 (Aug. 2009)).*
Subramanian et al. (MicroRNA expression signature of human sarcomas, Oncogene (2007), 1-12).*
Baoutz et al. (MicroRNAs regulate the expression of the alternative splicing factor nPTB during muscle development, Genes & Development 21:71-84, 2007).*
Jiang et al. (Real-time expression profiling of microRNA precursors in human cancer cell lines, Nucleic Acids Research, 2005, vol. 33, No. 17 Nucleic Acids Research, 2005, vol. 33, No. 17, 5394-5403).*
Yan et al. (MicroRNA-1/206 Targets c-Met and Inhibits Rhabdomyosarcoma Development, The Journal of Biological Chemistry vol. 284, No. 43, pp. 29596-29604, Oct. 23, 2009).*
Wei et al. (microRNA Profiling Identifies Cancer-Specific and Prognostic Signatures in Pediatric Malignancies, Clin Cancer Res 2009;15(17) Sep. 1, 2009).*
Lu et al. (MicroRNA expression profiles classify human cancers, Nature Letters, vol. 435, No. 9, Jun. 2005).*
Calin et al. (MicroRNA signatures in human cancers, Nature Reviews Cancer, vol. 6, Nov. 2006).*
Mitchell et al. (Circulating microRNAs as stable blood-based markers for cancer detection, PNAS, vol. 105, No. 30, Jul. 29, 2008, 10513-10518).*
Dongsheng Yan et al., "MicroRNA-1/206 Targets *c-Met* and Inhibits Rhabdomyosarcoma Development," Journal of Biological Chemistry 2009, vol. 284, No. 43, pp. 29596-29604.
John J. McCarthy, "MicroRNA-206: the skeletal muscle-specific myomiR," Biochimica Biophys Acta, 2008, vol. 1779, No. 11, pp. 682-691 (pp. 1-23).
M. Miyachi, et al., "Circulating muscle-specific microRNA miR-206 is a novel marker for rhabdomyosarcoma," http://www.researchgate.net/publication/45582591_Circulating_muscle-specific_microRNA_miR-206_as_a_potential_diagnostic_marker_for_rhabdomyosarcoma>The Japanese Society of Pediatric Hematology, Japanese Society of Pediatric Oncology, Japanese Society of Pediatric Oncology Nursing, Children's Cancer Association of Japan Kokai Symposium Program Sokaigo, 2010, vol. 52nd-26th-8th-15th, p. 194, a cover page and English translation thereof.
Mitsuru Miyachi et al., "Circulating muscle-specific microRNA, miR-206, as a potential diagnostic marker for rhabdomyosarcoma," Biochemical and Biophysical Research Communications, 2010, vol. 400, No. 1, pp. 89-93.
Takahiro Goto et al., "Prediction of *MYCN* Amplification in Neuroblastoma Using Serum DNA and Real-Time Quantitative Polymerase Chain Reaction," Journal of Clinical Oncology, 2005, vol. 23, No. 22, pp. 5205-5210.
Shigeki Yagyu et al., "Circulating Methylated-*DCR2* Gene in Serum as an Indicator of Prognosis and Therapeutic Efficacy in Patients with *MYCN* Nonamplified Neuroblastoma," Clinical Cancer Research, 2008, vol. 14, No. 21, pp. 7011-7019 and a cover page.
George A. Calin et al., "MicroRNA signatures in human cancers," Nature Reviews Cancer, 2006, vol. 6, pp. 857-866.

(Continued)

*Primary Examiner* — Stephanie K Mummert
*Assistant Examiner* — Aaron Priest
(74) *Attorney, Agent, or Firm* — Locke Lord LLP; James E. Armstrong, IV; Gabriel J. McCool

(57) ABSTRACT

The present invention provides a method for detecting rhabdomyosarcoma comprising evaluating expression of at least one kind of miRNA selected from the group consisting of hsa-miR-1, hsa-miR-133a, hsa-miR-133b, and hsa-miR-206 in a sample derived from body fluid.

16 Claims, 12 Drawing Sheets

(56) References Cited

OTHER PUBLICATIONS

Jun Lu et al., "MicroRNA expression profiles classify human cancers," Nature, 2005, vol. 435, pp. 834-838.

Jun S. Wei et al., "MicroRNA Profiling Identifies Cancer-Specific and Prognostic Signatures in Pediatric Malignancies," Clinical Cancer Research, 2009, vol. 15, No. 17, pp. 5560-5568 and a cover page.

S Subramanian et al., "MicroRNA expression signature of human sarcomas," Oncogene, 2007, pp. 1-12.

E K O Ng et al, "Differential expression of microRNAs in plasma of patients with colorectal cancer: a potential marker for colorectal cancer screening," Gut, 2009, vol. 58, pp. 1375-1381 and a cover page.

Patrick S. Mitchell et al., "Circulating microRNAs as stable blood-based markers for cancer detection," PNAS, 2008, vol. 105, No. 30, pp. 10513-10518.

Charles H. Lawrie et al., "Detection of elevated levels of tumour-associated microRNAs in serum of patients with diffuse large B-cell lymphoma," British Journal of Haematology, 2008, vol. 141, pp. 672-675.

Yusuke Yamamoto et al., "MicroRNA-500 as a potential diagnostic marker for hepatocellular carcinoma," Biomarkers, 2009, vol. 14, No. 7, pp. 529-538 and a cover page.

International Search Report dated Jun. 21, 2011, issued for PCT/JP2011/058843.

* cited by examiner

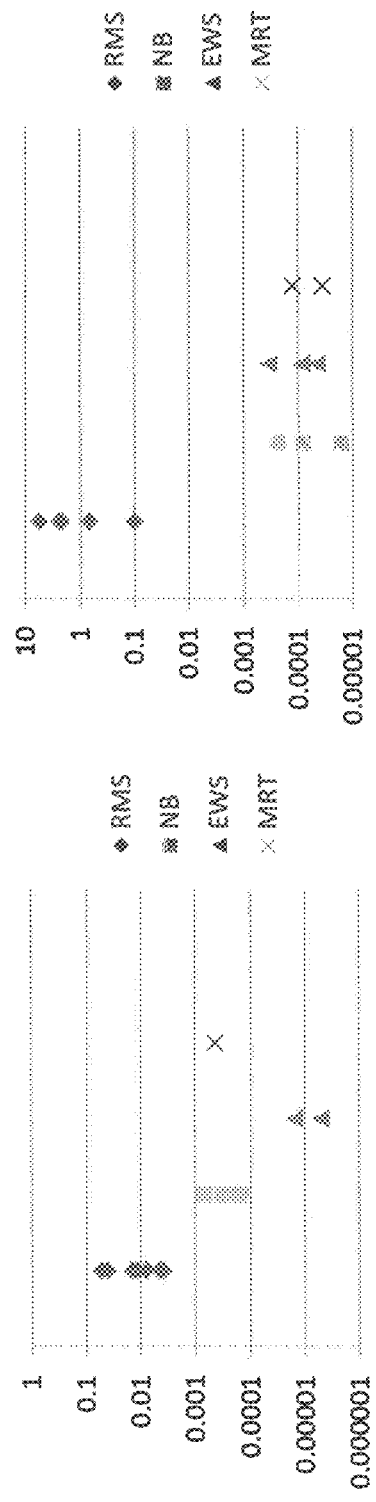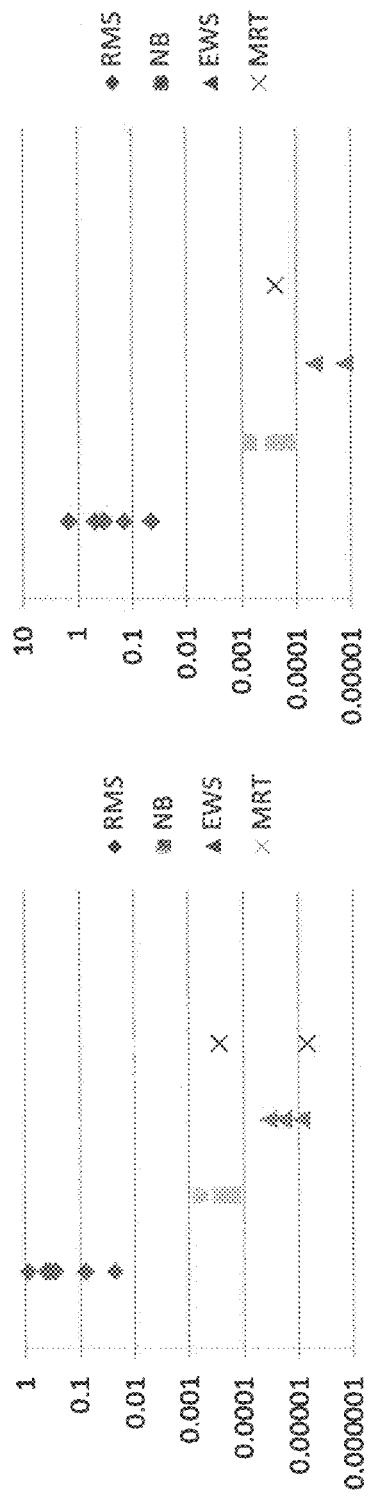

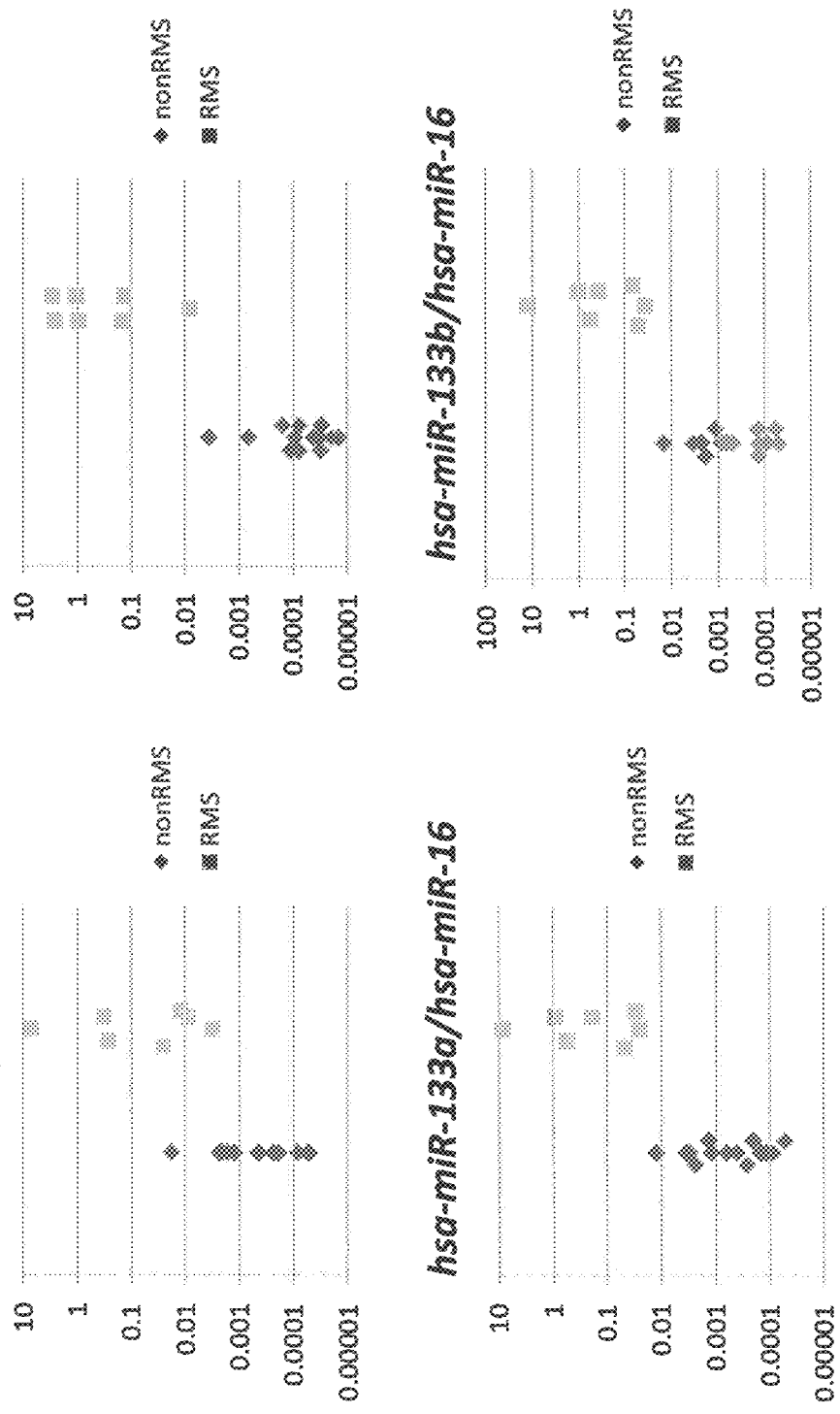

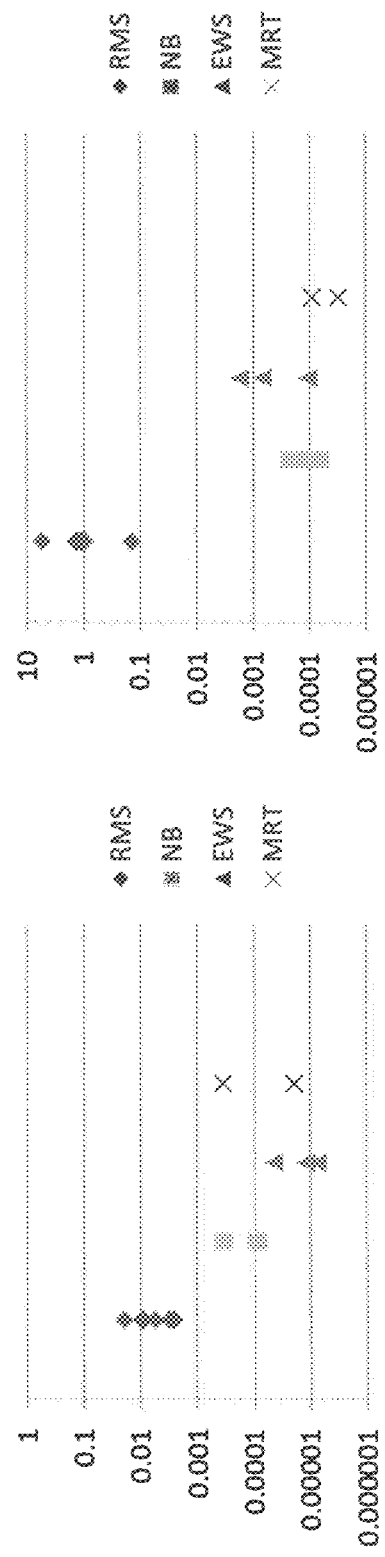
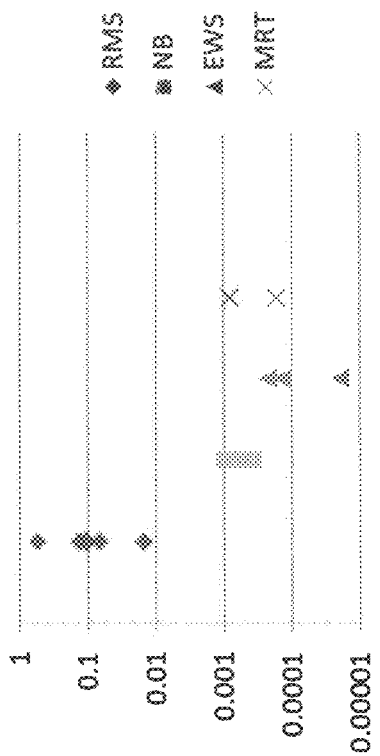
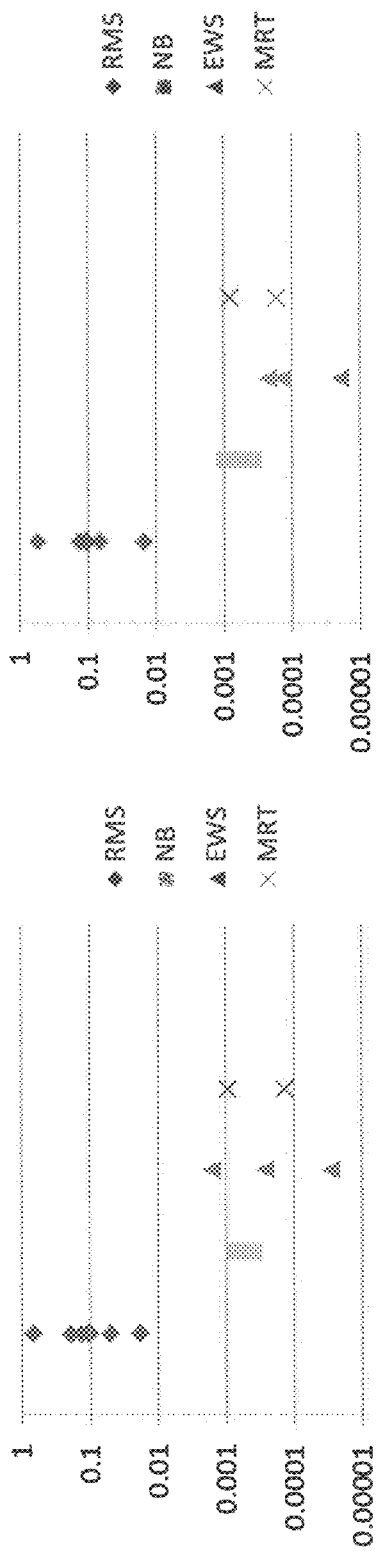
Fig. 3

Fig. 9
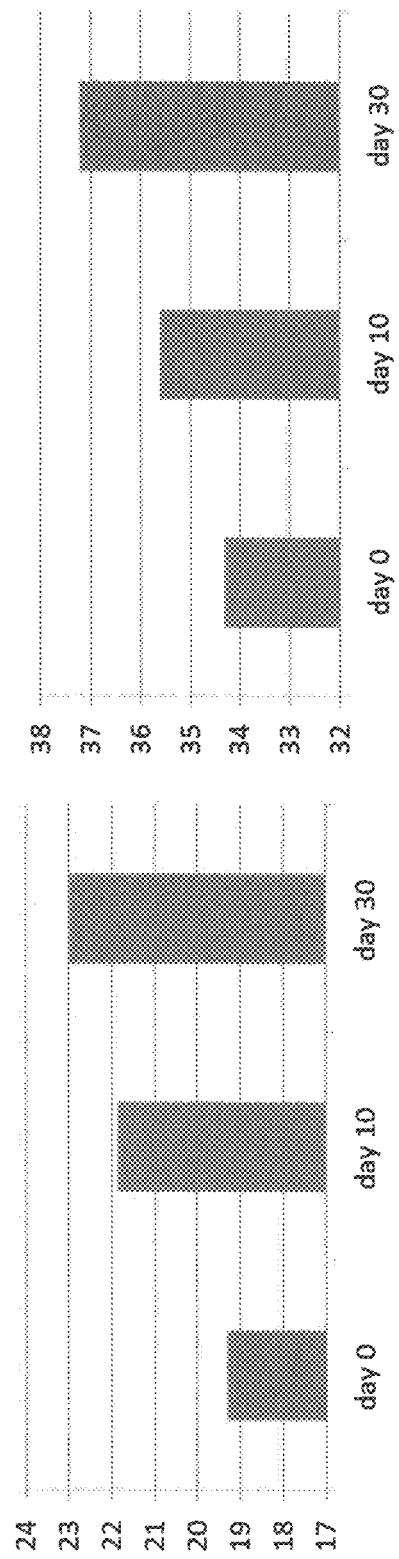
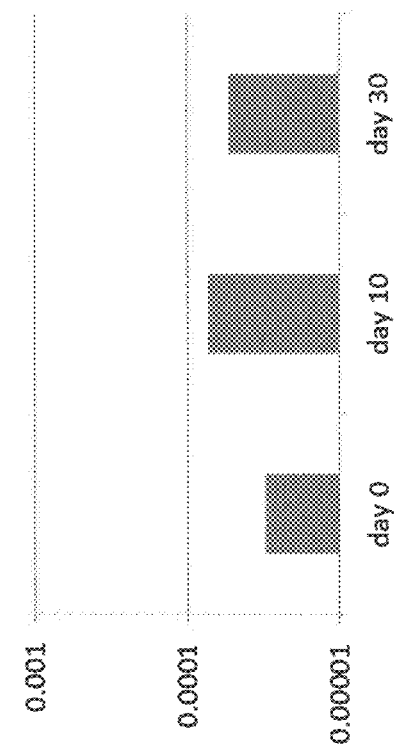

SEQUENCE LISTING

```
<160> NUMBER OF SEQ ID NOS: 5

<210> SEQ ID NO 1
<211> LENGTH: 22
<212> TYPE: RNA
<213> ORGANISM: Homo sapiens

<400> SEQUENCE: 1
uggaauguaa agaaguaugu au                                              22

<210> SEQ ID NO 2
<211> LENGTH: 22
<212> TYPE: RNA
<213> ORGANISM: Homo sapiens

<400> SEQUENCE: 2
uuuggucccc uucaaccagc ug                                              22

<210> SEQ ID NO 3
<211> LENGTH: 22
<212> TYPE: RNA
<213> ORGANISM: Homo sapiens

<400> SEQUENCE: 3
uuuggucccc uucaaccagc ua                                              22

<210> SEQ ID NO 4
<211> LENGTH: 22
<212> TYPE: RNA
<213> ORGANISM: Homo sapiens

<400> SEQUENCE: 4
uggaauguaa ggaagugugu gg                                              22

<210> SEQ ID NO 5
<211> LENGTH: 22
<212> TYPE: RNA
<213> ORGANISM: Homo sapiens
```

-continued

```
<400> SEQUENCE: 5
uagcagcacg uaaauauugg cg                                                22
```

METHOD FOR DETECTING RHABDOMYOSARCOMA USING SAMPLE DERIVED FROM BODY FLUID

TECHNICAL FIELD

The present invention relates to a method for detecting rhabdomyosarcoma using a sample derived from body fluid.

BACKGROUND ART

The inventors have addressed the development of a non-invasive diagnostic technique using free DNA derived from a tumor in serum (Non-patent Documents 1 and 2). In recent years, the existence of microRNAs (miRNAs), non-coding RNAs that are not translated into proteins, has been confirmed. It has been reported that their expression profiles are tissue- or tumor-specific (Non-patent Documents 3 and 4). In pediatric cancers as well, it is reported in a study using cell lines (Non-patent Document 5) that expression profiles differ depending on the tumor. In rhabdomyosarcoma, which is the most common soft-tissue sarcoma in pediatric cancers, it is revealed that the expression of miRNAs specifically expressed in muscle is increased (Non-patent Documents 5 and 6). Additionally, it is also revealed that miRNAs of tumor origin exist in serum. Thus, the utility of miRNAs as biomarkers is suggested in colorectal cancer, lymphoma, prostatic cancer, liver cancer, and the like (Non-patent Documents 7-10).

PRIOR ART DOCUMENTS

Non-patent Documents

Non-Patent Document 1:
Gotoh, et al. J Clin Oncol 23: 5205-5210, 2005
Non-Patent Document 2:
Yagyu, et al. Clin Cancer Res 14: 7011-7019, 2008
Non-Patent Document 3:
Calin G A, et al. Nat Rev Cancer; 6: 857-866, 2006
Non-Patent Document 4:
Lu J, et al. Nature; 435: 834-838, 2005
Non-Patent Document 5:
Wei J S, et al. Clin Cancer Res; 15: 5560-5568, 2009
Non-Patent Document 6:
Subramanian S, et al. Oncogene; 27: 2015-2026, 2008
Non-Patent Document 7:
Ng EKO, et al. Gut; 58: 1375-1381, 2009
Non-Patent Document 8:
Mitchell P S, et al. PNAS; 105: 10513-10518, 2008
Non-Patent Document 9:
Lawrie C H, et al. Br J Haematol; 141: 672-675, 2008
Non-Patent Document 10:
Yamamoto Y, et al. Biomarkers; 14: 529-538, 2009

DISCLOSURE OF THE INVENTION

Problem to be Solved by the Invention

An object of the present invention is to provide a method of detecting rhabdomyosarcoma that is difficult to diagnose easily.

Means for Solving the Problem

The inventors quantified hsa-miR-1, hsa-miR-133a, hsa-miR-133b and hsa-miR-206, a group of miRNAs specifically expressed in muscle, in samples derived from body fluids of pediatric tumor patients; and investigated the possibility of non-invasive diagnosis of rhabdomyosarcoma. As a result, the inventors discovered that rhabdomyosarcoma was detectable by these miRNAs.

The present invention provides the following methods for detecting rhabdomyosarcomas.
1. A method for detecting rhabdomyosarcoma comprising evaluating expression of at least one kind of miRNA selected from the group consisting of hsa-miR-1, hsa-miR-133a, hsa-miR-133b, and hsa-miR-206 in a sample derived from body fluid.
2. The method for detecting rhabdomyosarcoma according to the above item 1, wherein the standard of the detection is a significant increase in an expression amount of the at least one selected from the group consisting of hsa-miR-1, hsa-miR-133a, hsa-miR-133b, and hsa-miR-206 in the sample derived from body fluid, compared to that of a normal subject.
3. The method for detecting rhabdomyosarcoma according to the above item 1, wherein the evaluating comprises evaluating expression of at least one kind of miRNA selected from the group consisting of hsa-miR-133a, hsa-miR-133b and hsa-miR-206.
4. The method for detecting rhabdomyosarcoma according to the above item 1, wherein the evaluating comprises evaluating expression of at least hsa-miR-206.
5. The method for detecting rhabdomyosarcoma according to the above item 1 detected by real-time PCR.
6. The method for detecting rhabdomyosarcoma according to the above item 1, wherein the body fluid is blood and the sample derived from body fluid is plasma or serum.

Effects of the Invention

Rhabdomyosarcoma is one of the tumors that are difficult to diagnose. However, according to the present invention, the detection of rhabdomyosarcoma, which has been thought impossible in the past, can be achieved using a sample of body fluid.

Regarding rhabdomyosarcoma, it is important for prognostic improvement to excise a rhabdomyosarcoma tumor completely before chemotherapy and radiotherapy; it is also important to make a tentative diagnosis preoperatively in order to determine an operation plan whose purpose is initial complete excision. The present invention enables faster and more accurate diagnosis of rhabdomyosarcoma, and improvement in the treatment results of rhabdomyosarcoma can be expected.

BRIEF DESCRIPTION OF THE DRAWINGS

FIG. 1 illustrates an increase in expression of muscle-specific microRNAs in rhabdomyosarcoma cell lines. The ordinate axis is a ratio of each muscle-specific miRNA to hsa-miR-16. RMS: rhabdomyosarcoma, NB: neuroblastoma, EWS: Ewing's sarcoma, MRT: malignant rhabdoid tumor.

FIG. 2 illustrates an increase in expression of muscle-specific microRNAs in rhabdomyosarcoma tumor samples. The ordinate axis is a ratio of each muscle-specific miRNA to hsa-miR-16. RMS: rhabdomyosarcoma, nonRMS: tumors other than rhabdomyosarcoma.

FIG. 3 illustrates expression amounts of hsa-miR-1, hsa-miR-206, hsa-miR-133a, and hsa-miR-133b in culture supernatants of the rhabdomyosarcoma cell lines. The ordinate axis is a ratio of muscle-specific miRNA to hsa-miR-16. RMS: rhabdomyosarcoma, NB: neuroblastoma, EWS: Ewing's sarcoma, MRT: malignant rhabdoid tumor.

FIG. 9 illustrates stability of miRNAs in human serum. The stability of serum microRNAs was studied in storage at 4° C. The Ct values of both hsa-miR-16 and hsa-miR-133b tend to gradually increase as storage time passes, and increased by 3 and 4 on day 30 (decrease to $1/16$ and $1/8$ as an absolute amount). On the other hand, no great change was observed in the ratio of hsa-miR-133b to hsa-miR-16.

MODES FOR CARRYING OUT THE INVENTION

Figure 4:
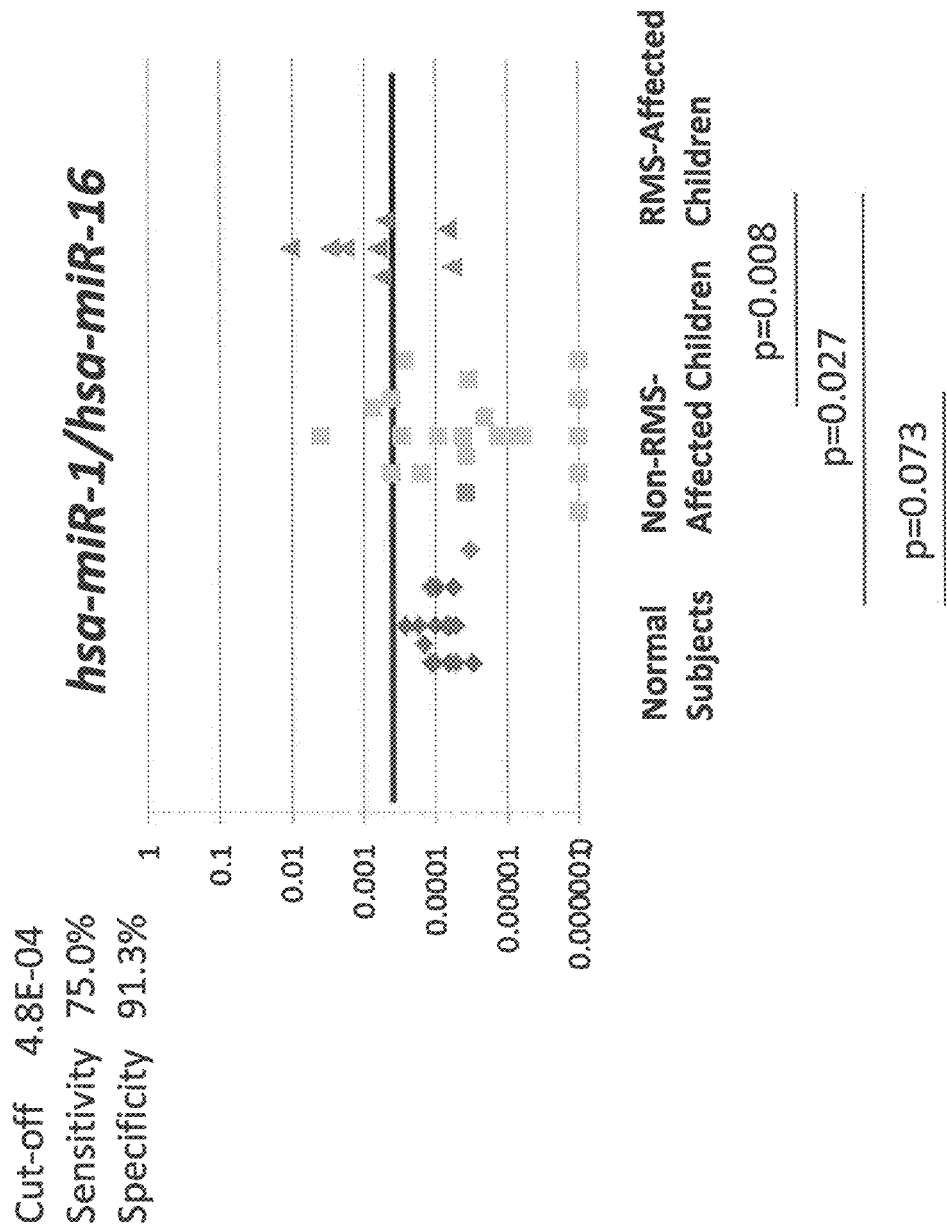
FIG. 4 is a comparison of serum hsa-miR-1 among normal subjects, cancer-affected children, and rhabdomyosarcoma—(RMS) affected children. The ordinate axis is a ratio of hsa-miR-1 to hsa-miR-16. RMS: rhabdomyosarcoma, nonRMS: tumors other than rhabdomyosarcoma.
Figure 5:
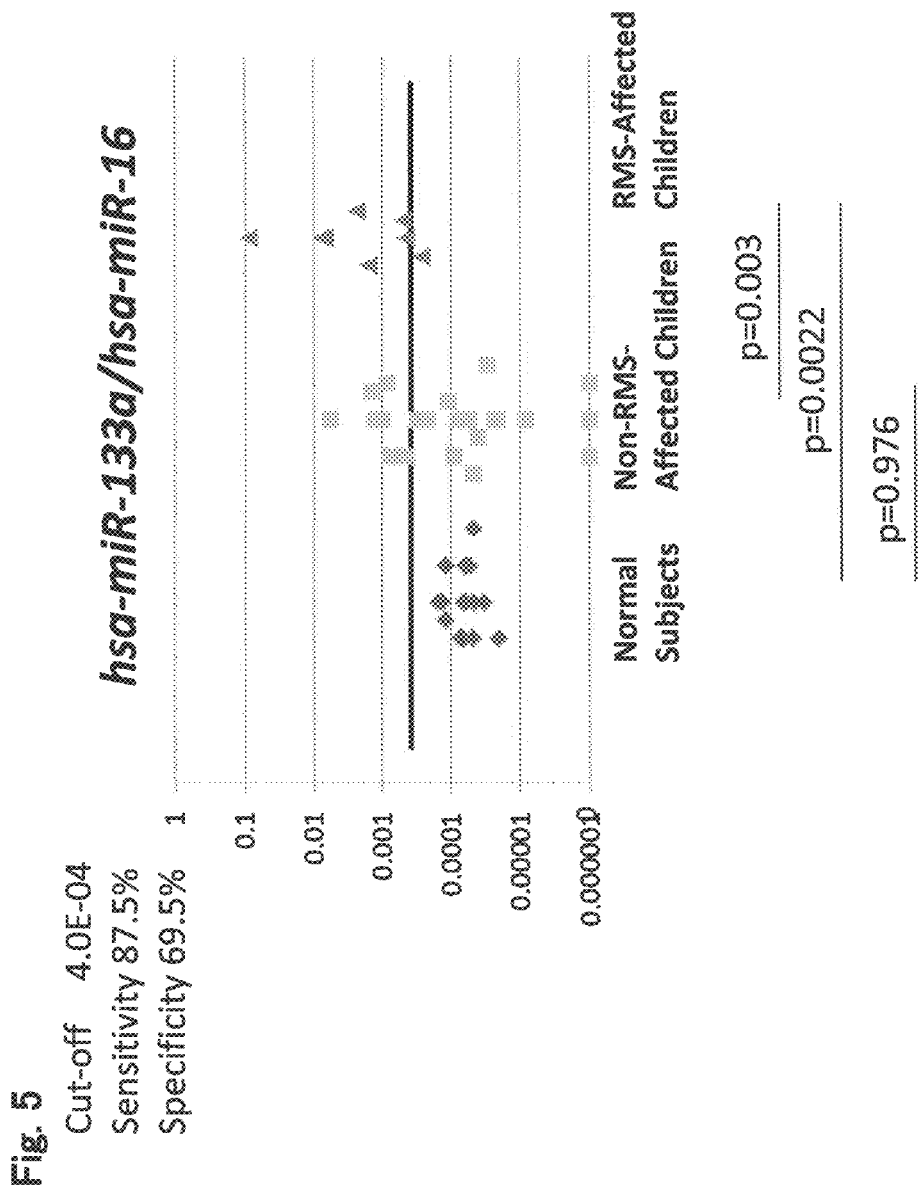
FIG. 5 is a comparison of serum hsa-miR-133a among normal subjects, cancer-affected children, and rhabdomyosarcoma—(RMS) affected children. The ordinate axis is a ratio of hsa-miR-133a to hsa-miR-16. RMS: rhabdomyosarcoma, nonRMS: tumors other than rhabdomyosarcoma.
Figure 6:
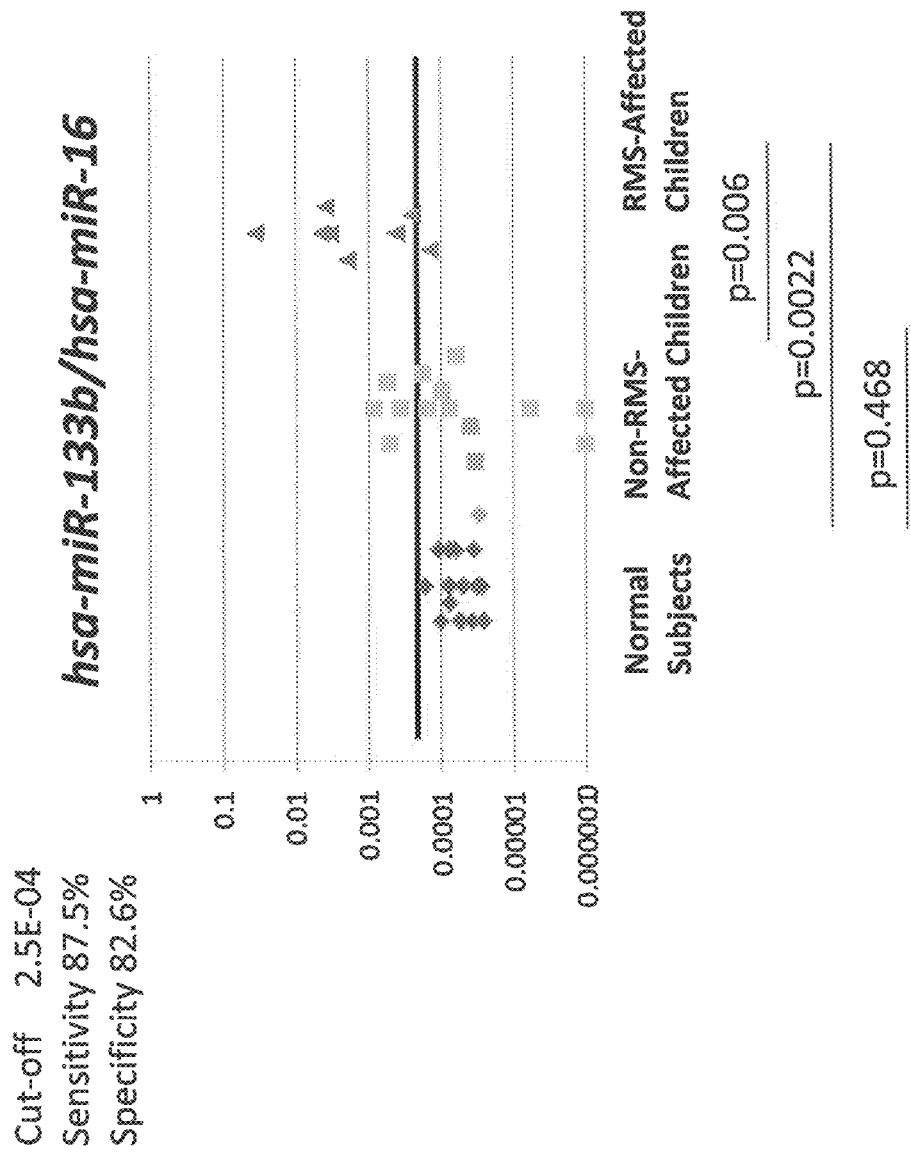
FIG. 6 is a comparison of serum hsa-miR-133b among normal subjects, cancer-affected children, and rhabdomyosarcoma—(RMS) affected children. The ordinate axis is a ratio of hsa-miR-133b to hsa-miR-16. RMS: rhabdomyosarcoma, nonRMS: tumors other than rhabdomyosarcoma.

The sequences of hsa-miR-1, hsa-miR-133a, hsa-miR-133b and hsa-miR-206, which are subjects to be detected in the present invention, are shown below. These sequences are indicated in Table 1 along with the sequence of hsa-miR-16, which is usable as an internal control due to its high expression and smaller variation between tissues.

TABLE 1

| miRNA | RNA Sequences | SEQ ID |
|---|---|---|
| hsa-miR-1 | UGGAAUGUAAAGAAGUAUGUAU | SEQ ID NO. 1 |
| hsa-miR-133a | UUUGGUCCCCUUCAACCAGCUG | SEQ ID NO. 2 |
| hsa-miR-133b | UUUGGUCCCCUUCAACCAGCUA | SEQ ID NO. 3 |
| hsa-miR-206 | UGGAAUGUAAGGAAGUGUGUGG | SEQ ID NO. 4 |
| hsa-miR-16 | UAGCAGCACGUAAAUAUUGGCG | SEQ ID NO. 5 |

As illustrated in FIG. 3, hsa-miR-1, hsa-miR-133a, hsa-miR-133b, and hsa-miR-206 are released to the culture supernatants of the rhabdomyosarcoma cell lines in a large amount, and tumor-derived cell-free miRNAs released from the inside of tumor cells are present. Tumor-derived, cell-free miRNAs are also present in body fluid in a human body. Thus, it is thought that such miRNA can be used for detection and diagnosis of rhabdomyosarcoma.

In the specification, body fluid includes blood, pleural effusion, ascites fluid, cerebrospinal fluid, urine, and the like. Blood is useful irrespective of the site of occurrence or the site of metastasis of rhabdomyosarcoma. However, when the site of occurrence or the site of metastasis is a urinary organ, urine is useful. When the site is a central nervous system, cerebrospinal fluid is useful. When the site is an abdominal cavity, ascites fluid is useful. When the site is a pleural cavity, pleural effusion is useful.

When blood is used as the body fluid, a blood sample (plasma or serum) is centrifuged at 18,000 g for 10 minutes, and the use of the supernatant is necessary to prevent the mixture of leukocytes or erythrocytes thereinto.

The miRNA used in the present invention can also be detected from a 20-year-old serum sample that was stored at −20° C., and it has sufficient stability in the serum to be used for the present invention (FIG. 9). For example, when the serum was stored for 30 days at 4° C., the amounts of hsa-miR-16 and hsa-miR-133b decreased to about $1/16$ and about $1/8$ as an absolute amount, respectively; however, no great change was observed in the ratio of hsa-miR-133b to hsa-miR-16.

Detection and quantification of miRNA can be carried out by reverse transcription of the sample containing miRNA to obtain cDNA, and conducting a suitable method such as quantitative real-time PCR of the cDNA. cDNA can be prepared by a reverse transcription reaction, using, for example, a TaqMan MicroRNA RT Kit (Applied Biosystems); mature microRNA specific RT primers of TagMan MicroRNA assays; and the like. The quantitative real-time PCR can be carried out using TagMan primers and probes of TagMan MicroRNA assays, and TagMan Universal PCR Master Mix.

In the detection of rhabdomyosarcoma, expression of muscle-specific miRNA significantly increases in a group of rhabdomyosarcoma at $p<0.05$.

As the miRNA to be measured, hsa-miR-206, which has the highest sensitivity and specificity, is considered to be useful. With respect to hsa-miR-133a, hsa-miR-133b and hsa-miR-206, correlation of a tumor with the microRNA amount in serum was observed.

In the rhabdomyosarcoma detection of the present invention, the ratio of muscle-specific miRNA (hsa-miR-1, hsa-miR-133a, hsa-miR-133b, and hsa-miR-206) to hsa-miR-16, i.e., muscle-specific miRNA/hsa-miR-16, is expected as a biomarker of body fluid, especially serum, at the time of diagnosing rhabdomyosarcoma.

According to the detection method of the present invention, rhabdomyosarcoma (RMS) is distinctly detectable from other children's tumors such as neuroblastoma (NB), Ewing's sarcoma (EWS), and malignant rhabdoid tumor (MRT). Conventionally, the distinction of RMS from these tumors was difficult. The present invention provides extremely effective means for specific detection of rhabdomyosarcoma.

Figure 8:
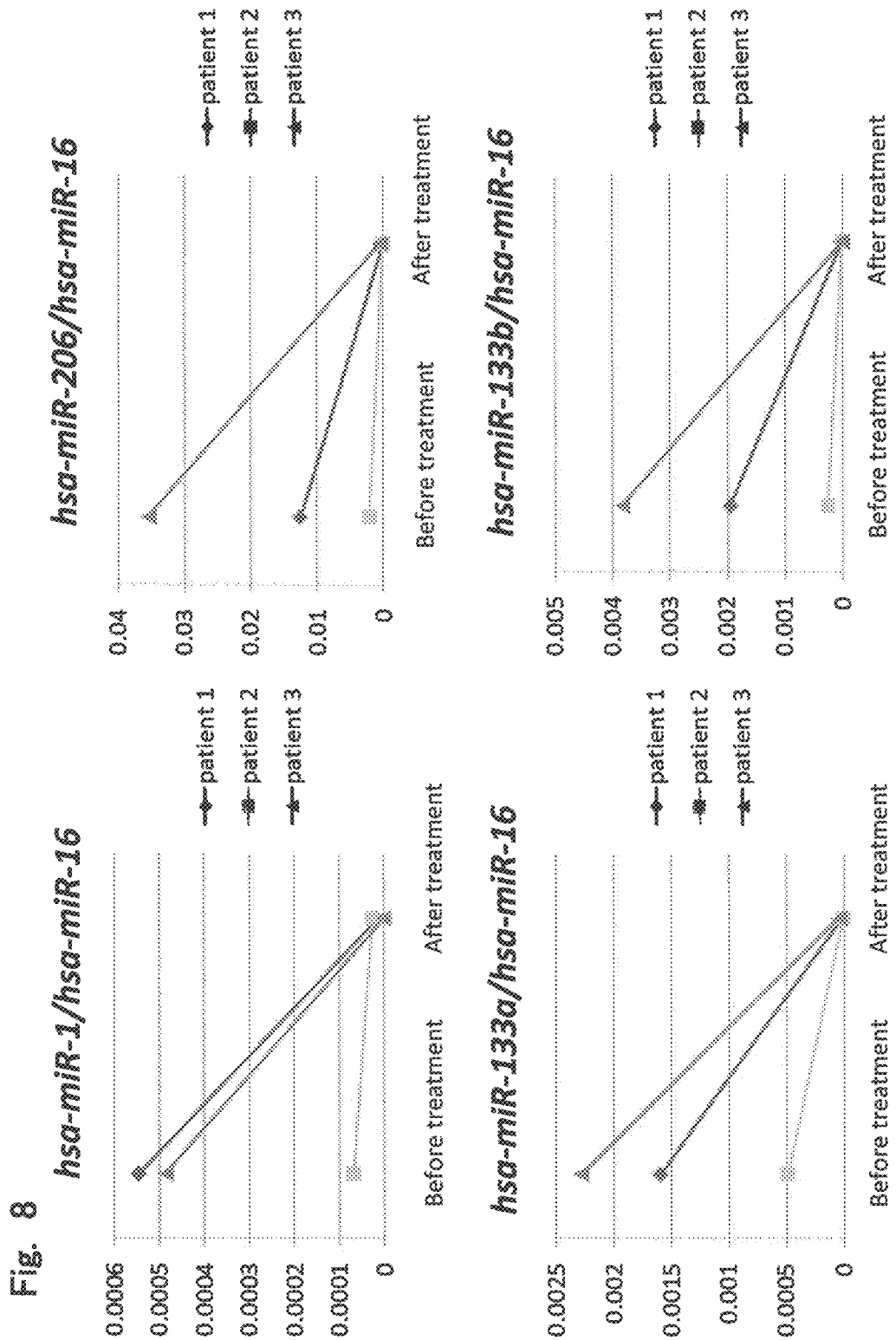
FIG. 8 illustrates a decrease in a ratio of each muscle-specific miRNA to hsa-miR-16 in RMS-affected children after the treatment. The ordinate axis is a ratio of the muscle-specific miRNA to hsa-miR-16.
Figure 10:
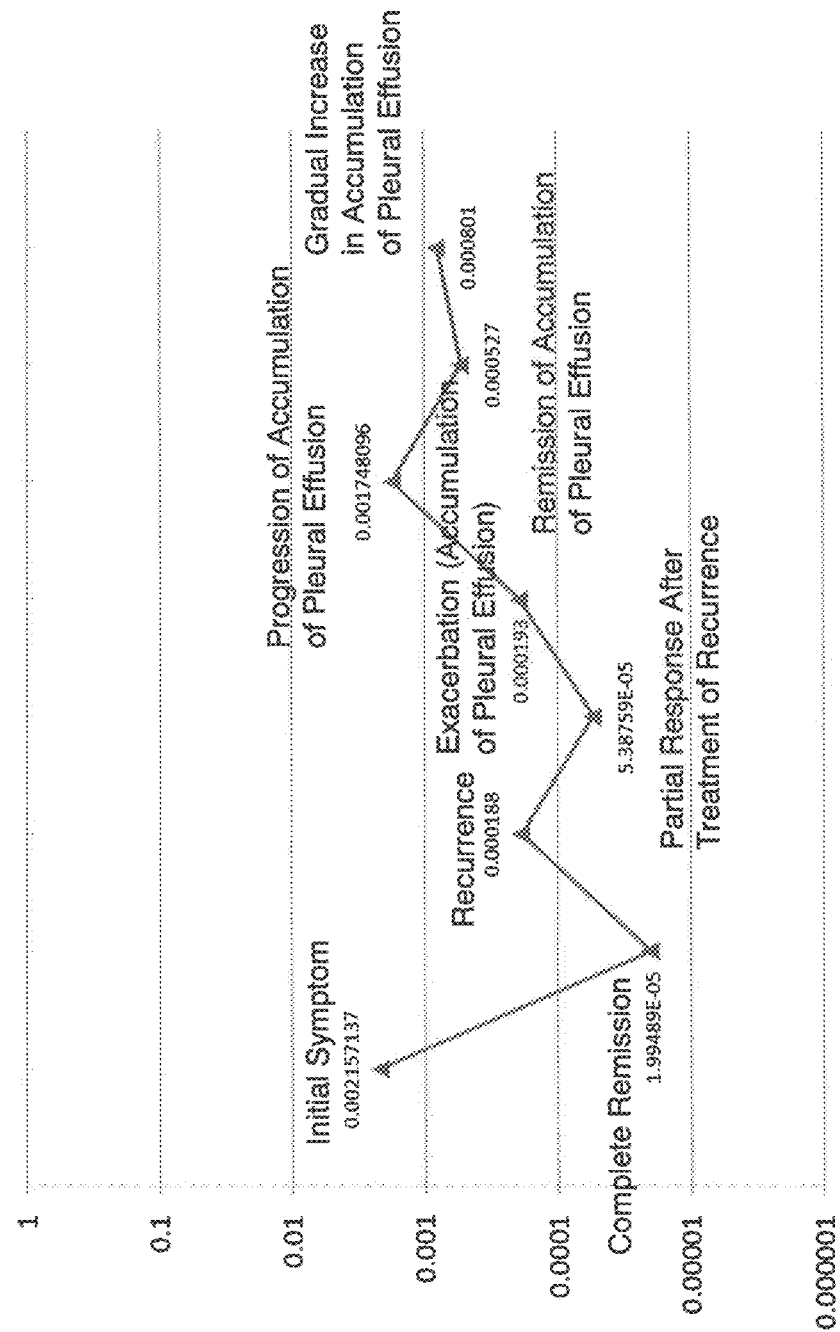
FIG. 10 illustrates the reflection of the muscle-specific miRNA in serum on the disease activity of rhabdomyosarcoma.
Figure 11:
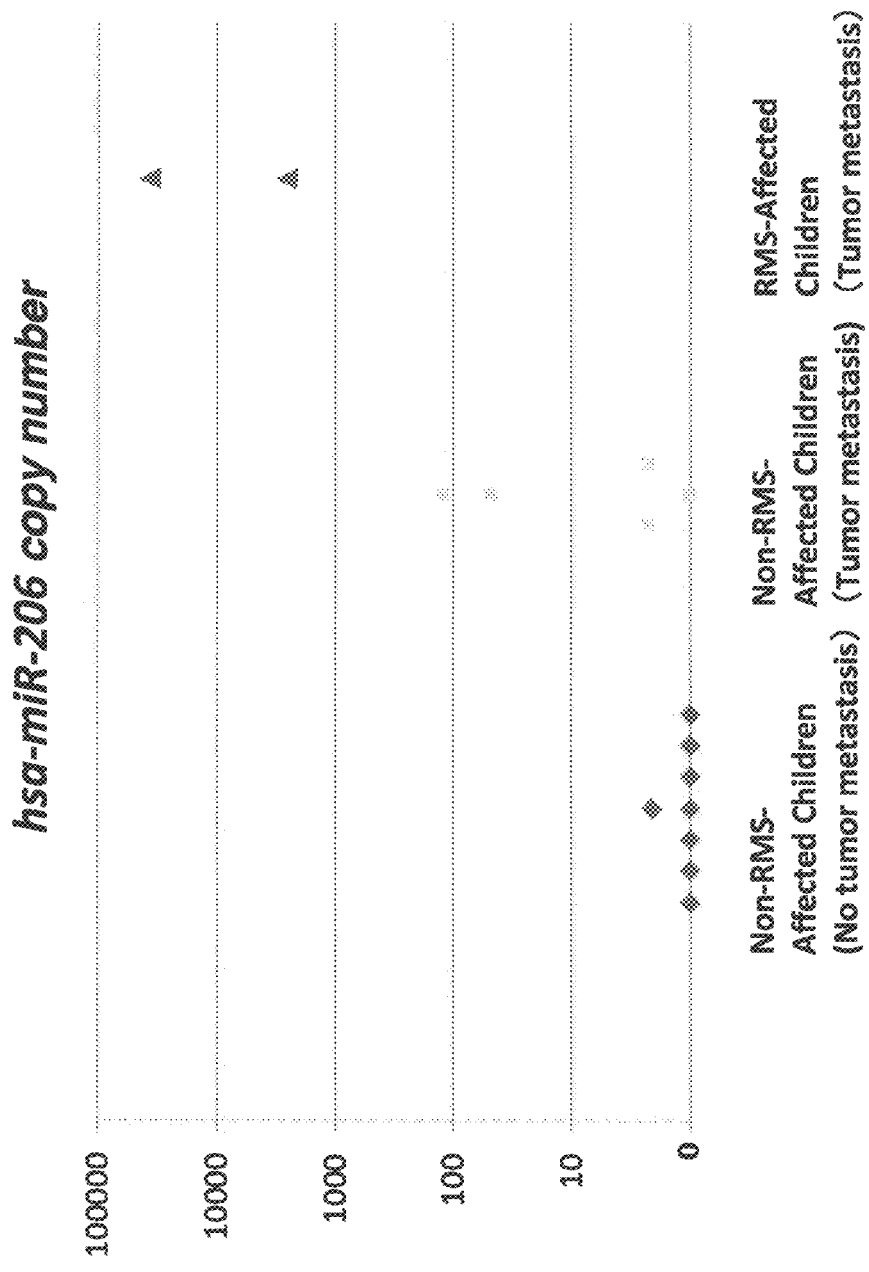
FIG. 11 illustrates the additional detection of the muscle-specific miRNA in body fluid (cerebrospinal fluid and pleural effusion) other than the serum of children with rhabdomyosarcoma.

Since the amount of the muscle-specific miRNA of the present invention is decreased after the treatment of rhabdomyosarcoma, it also becomes an index of disease activity and therapeutic response (FIGS. 8, 10, and 11).

The present invention will be described in more detail in the following examples, but is not limited to these examples.

EXAMPLES

Example 1

1. Method
Cell lines, Tumor Samples and Serums
Studies were conducted using the following held by the Department of Pediatrics, Kyoto Prefectural University of Medicine:

16 cell lines (7 rhabdomyosarcoma, 4 neuroblastoma, 3 Ewing's sarcoma, 2 malignant rhabdoid tumor);

21 tumor samples (7 rhabdomyosarcoma, 4 undifferentiated sarcoma, 2 Wilms' tumor, 2 neuroblastoma, 1 Ewing's sarcoma, 1 malignant rhabdoid tumor, 1 adrenal cancer, 1 retinoblastoma, 1 alveolar soft-tissue sarcoma, 1 osteosarcoma);

48 serum samples (8 rhabdomyosarcoma, 3 neuroblastoma, 2 Wilms' tumor, 2 Ewing's sarcoma, 2 hepatoblastoma, 2 retinoblastoma, 2 osteosarcoma, 2 undifferentiated sarcoma, 1 malignant rhabdoid tumor, cell alveolar soft-tissue sarcoma 1, 1 adrenal cancer, 1 pancreas blastocytoma, 1 teratoid tumor, 1 acute lymphoblastic leukemia, and 1 Langerhans cell histiocytosis, 1 neuroglioma, and 17 normal subject volunteers); and 15 body fluid samples (2 rhabdomyosarcoma (1 cerebrospinal fluid and 1 pleural effusion), 3 neuroblastoma (1 cerebrospinal fluid, 1 pleural effusion and 1 ascites fluid), 3 medulloblastoma (3 cerebrospinal fluid), 1 ependymoma (1 cerebrospinal fluid), retinoblastoma 1 (1 cerebrospinal fluid), 1 malignant rhabdoid tumor (1 cerebrospinal fluid), 1 Wilms' tumor (1 cerebrospinal fluid), 1 germ cell tumor (1 ascites fluid), 1 chylothorax (pleural effusion 1), and 1 autoimmune disease (1 cerebrospinal fluid)).

Extraction of RNA

A total RNA containing miRNAs was extracted using a mirVana PARIS Kit (Ambion). Regarding culture supernatant of cell lines or serums, these are further centrifuged at 15,000 rpm for 10 minutes to remove cell components, and the supernatants were used.

Reverse Transcription Reaction

The reverse transcription reaction was performed using TaqMan MicroRNA RT kit (Applied Biosystems) and primers for a mature miRNA-specific reverse transcription reaction of TaqMan MicroRNA assays (Applied Biosystems).

Quantitative Real-Time PCR

Quantitative real-time PCR was performed using a reverse transcripted cDNA solution, and the primers and probes of TaqMan MicroRNA assays. In samples other than body fluid, there was little variation in expressions among tissues. Thus, hsa-miR-16 that is expressed at a high level was used as an internal control, and expression of muscle-specific miRNA was normalized for quantification using the ΔΔCt method. In the body fluid sample, the expression of hsa-miR-16 was not constant. Thus, the standard curve was prepared using a synthetic miRNA that has a known copy number, and quantification was conducted using an absolute quantity. The copy number of hsa-miR-206 per 1 μl serum was calculated and compared. The sequences of muscle-specific miRNAs (hsa-miR-1, 133a, 133b and 206) and hsa-miR-16 are shown in Table 1.

Statistical Analysis

The expression of miRNA in serum was compared using the Mann-Whitney U-test. Correlation of a tumor with expression of miRNA in serum was examined using the Spearman's rank correlation coefficient. Every test was a two-sided test, and a p less than ($p<0.05$) was regarded as significantly different.

Statistical Analysis

The expression of miRNA in serum was compared using the Mann-Whitney U-test. Correlation of a tumor with expression of miRNA in serum was examined using the Spearman's rank correlation coefficient. Every test was a two-sided test, and a p less than ($p<0.05$) was regarded as significantly different.

2. Result

Expression of Muscle-specific miRNAs in Cell Lines

In the study of the cell lines, expression of muscle-specific miRNAs in the rhabdomyosarcoma cell lines (n=7) increased compared with those in the cell lines of neuroblastoma (n=4), Ewing's sarcoma (n=3), and malignant rhabdoid tumor (n=2) (FIG. 1).

Expression of Muscle-specific miRNA in Clinical Tumor Samples

In the study of the clinical tumor samples, expression of muscle-specific miRNAs increased in the rhabdomyosarcoma tumor samples (n=7) compared with those in other pediatric cancer tumor samples (n=14) (FIG. 2).

Expression of Muscle-specific miRNAs in Culture Supernatants of the Cell Lines

In the study of culture supernatants of the cell lines, expression of muscle-specific miRNAs increased in the culture supernatants (n=7) of the rhabdomyosarcoma cell lines compared with the culture supernatants of neuroblastoma (n=4), Ewing's sarcoma (n=3), and malignant rhabdoid tumor (n=2) (FIG. 3).

Expression of Muscle-Specific miRNAs in Serums

Figure 7:
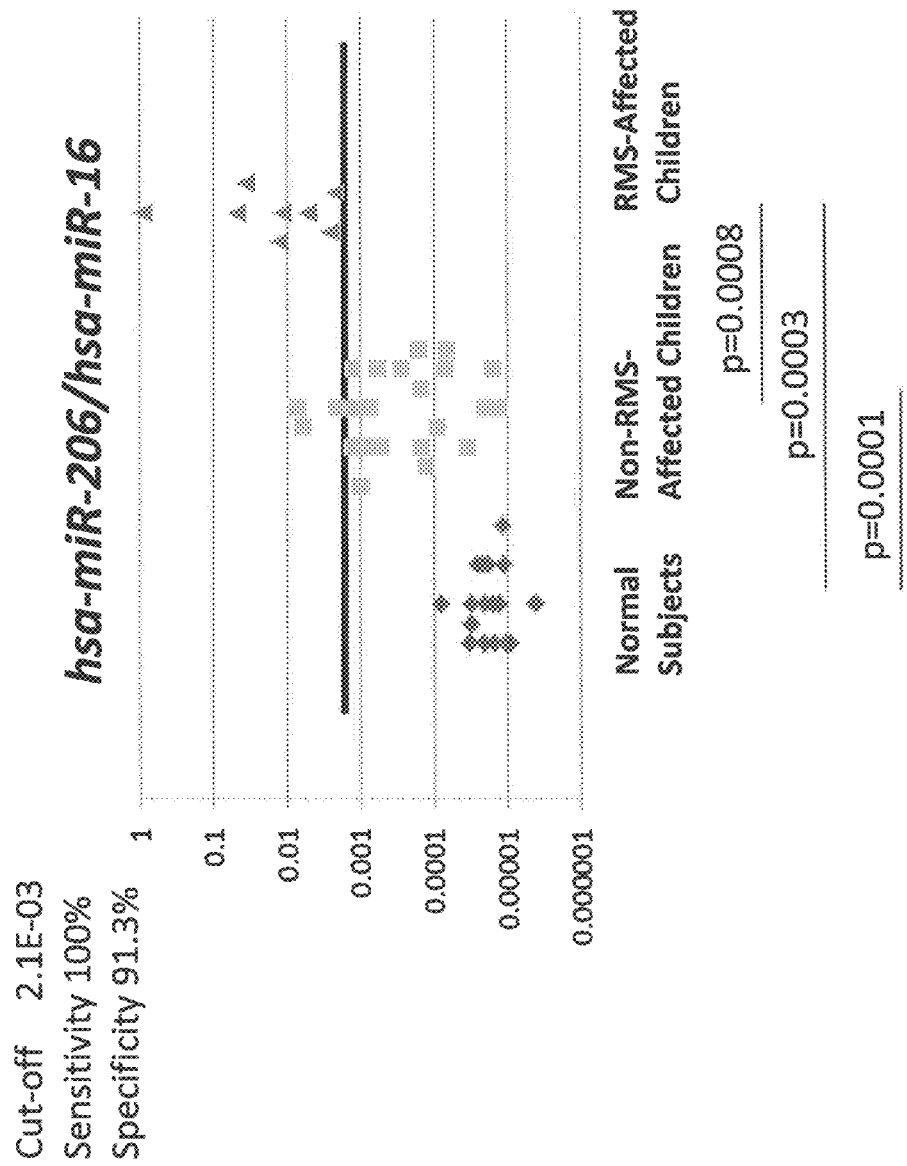
FIG. 7 is a comparison of serum hsa-miR-206 among normal subjects, cancer-affected children, and rhabdomyosarcoma—(RMS) affected children. The ordinate axis is a ratio of hsa-miR-206 to hsa-miR-16. RMS: rhabdomyosarcoma, nonRMS: tumors other than rhabdomyosarcoma.

In the study of serum, in the serums (n=8) of children affected with rhabdomyosarcoma, the expression of muscle-specific miRNAs increased with statistically significant difference compared with the serums of children affected with other pediatric cancers (n=23) and the serums of normal subject volunteers (n=17) (FIGS. 4-7). When the cut-off value was set, and sensitivity and specificity were calculated using the ROC curve, hsa-miR-206 showed the highest sensitivity and specificity; the sensitivity was 100%, and the specificity was 91.3% (FIG. 7). With respect to the subjects from whom the samples of both a tumor and serum were obtained, correlation of the expression of miRNAs was studied. The results showed that hsa-miR-1 was not statistically significant; however, there was a tendency to correlate (p=0.0793), and a significant correlation was observed in hsa-miR-133a, 133b, and 206 (Table 2). In addition, in the three cases where a pair of serum before and after the treatment was obtained, change in expression of muscle-specific miRNAs due to the treatment was examined. After the treatment, each value was less than the cut-off value, and the expression was decreased to a level similar to that of the normal subject volunteers (FIG. 8). The muscle-specific miRNAs in serum increase or decrease reflecting the condition of rhabdomyosarcoma. When the treatment was successful, the expression decreased. At the time of recurrence and exacerbation, the expression increased (FIG. 10).

TABLE 2

| hsa-miRNA | Rs | P value |
|---|---|---|
| 1 | 0.48417 | 0.0793 |
| 133a | 0.544 | 0.044 |
| 133b | 0.557 | 0.038 |
| 206 | 0.780 | 0.001 |

Expression of Muscle-Specific miRNAs in Body Fluid

Figure 12:
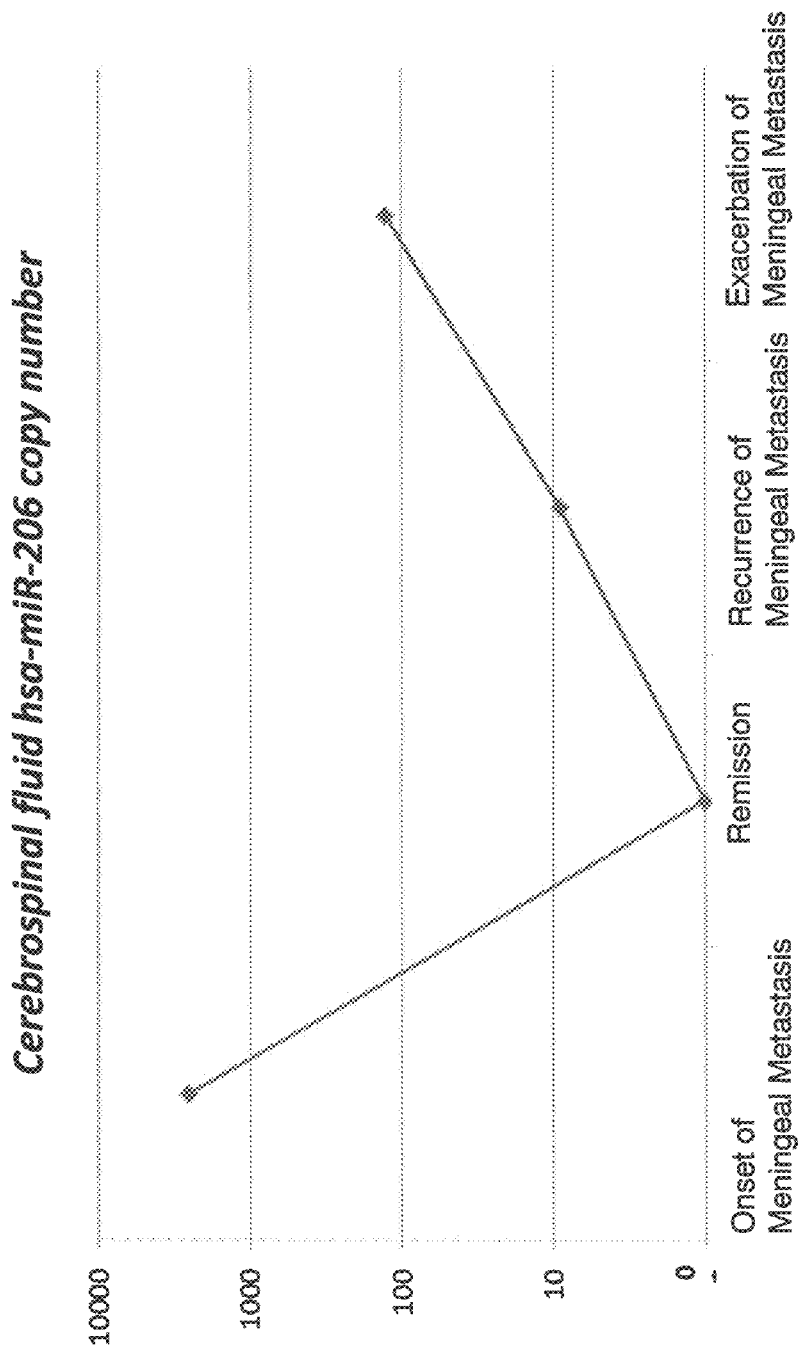
FIG. 12 illustrates the reflection of the muscle-specific miRNA in body fluid on the condition of rhabdomyosarcoma.

Additionally, in body fluid other than serum, such as cerebrospinal fluid and pleural effusion, the expression of muscle-specific miRNAs were of high values in the rhabdomyosarcoma patients (n=2) compared with those of the non-rhabdomyosarcoma patients (n=13) (FIG. 11). In the cerebrospinal fluid of the rhabdomyosarcoma patient who showed the symptoms of meningeal carcinomatosis as well, the expression varied reflecting the disease activity and therapeutic response. When the treatment was successful, the expression decreased. At the time of recurrence and exacerbation, the expression increased (FIG. 12).

3. Discussion

The expression of muscle-specific miRNAs increased in both the cell lines of rhabdomyosarcoma, and in the clinical tumor samples. These results did not contradict the fact that rhabdomyosarcoma is a tumor originating in undifferentiated myocyte. The muscle-specific miRNAs were also detectable from a culture supernatant of the cell lines in which cell components are removed. The expression of the muscle-specific miRNAs increased most in rhabdomyosarcoma. This suggests that the muscle-specific miRNAs are released outside the cells. In combination with the results of the clinical tumor samples, it was considered that the muscle-specific miRNA also exists in a large amount in the serum of rhabdomyosarcoma patients.

In the studies of serum, the expression of any muscle-specific miRNA was significantly increased in rhabdomyosarcoma patients' serums, and the expression was considered useful for the preoperative diagnosis of rhabdomyosarcoma. In particular, it was believed that hsa-miR-206 is the most useful as a biomarker because the sensitivity was 100% and the specificity was 91.3%. In addition, a correlation was observed between the clinical tumor sample and the expression amount of miRNAs in serum. Further, the expression of muscle-specific miRNAs is decreased to a level similar to that of the normal subject volunteers after the treatment. This suggests that miRNAs detected in serum is derived from a tumor. In body fluid other than serum as well, the expressions of muscle-specific miRNAs were of high values in the rhabdomyosarcoma patients, and the expressions changed depending on the disease activity and therapeutic response.

Although rhabdomyosarcoma is the most common soft-tissue sarcoma in children, currently, there is no biomarker that can be measured in a blood test. Meanwhile, since the existence of the residual tumor after a primary operation is an adverse prognostic factor, if the tentative diagnosis of rhabdomyosarcoma is made before the primary operation, an operation plan whose purpose is total extirpation is possible. Thus, the existence of the non-invasive biomarker that leads to the preoperative diagnosis of rhabdomyosarcoma is important. The muscle-specific miRNAs examined this time are believed to be novel biomarkers that make a preoperative diagnosis of rhabdomyosarcoma possible with high sensitivity and specificity, and that can contribute to a prognostic improvement.

The invention claimed is:

1. A method for detecting or diagnosing a rhabdomyosarcoma in a subject suspected of having a rhabdomyosarcoma comprising:
  quantifying expression of hsa-miR-1 in a first sample which is derived from a body fluid that is obtained from the subject suspected of having a rhabdomyosarcoma,
  quantifying expression of hsa-miR-1 in a second sample which is derived from a body fluid that is obtained from a normal subject; and
  comparing expression of hsa-miR-1 in the first sample with expression in the second sample,
  wherein detecting or diagnosing a rhabdomyosarcoma is obtained when there is increased expression of hsa-miR-1 in the first sample with respect to the second sample, and
  wherein expression is detected by real-time PCR and wherein the increased expression is evaluated is evaluated by having a P of less than 0.08 in a statistical test.

2. The method for detecting or diagnosing a rhabdomyosarcoma according to claim 1, wherein each of said steps of quantifying expression of hsa-miR-1 in a first and second sample further comprises quantifying expression of hsa-miR-206, wherein hsa miR 206 has statistically significant increased expression by having a P of less than 0.05 in a statistical test.

3. The method for detecting or diagnosing a rhabdomyosarcoma according to claim 1, wherein each of said steps of quantifying expression of hsa-miR-1 in a first and second sample further comprises quantifying the expression of one or more additional miRNAs selected from the group consisting of hsa-miR-133a and hsa-miR-133b, wherein the one or more additional miRNAs have statistically significant increased expression by having a P of less than 0.05 in a statistical test.

4. The method for detecting or diagnosing a rhabdomyosarcoma according to claim 2, wherein each of said steps of quantifying expression of hsa-miR-1 in a first and second sample further comprises quantifying the expression of one or more additional miRNAs selected from the group consisting of hsa-miR-133a and hsa-miR-133b, wherein the one or more additional miRNAs have statistically significant increased expression by having a P of less than 0.05 in a statistical test.

5. The method for detecting or diagnosing a rhabdomyosarcoma according to claim 1, wherein the body fluid is blood and the sample derived from the body fluid is plasma or is serum.

6. The method for detecting or diagnosing a rhabdomyosarcoma according to claim 2, wherein the body fluid is blood and the sample derived from the body fluid is plasma or is serum.

7. The method for detecting or diagnosing a rhabdomyosarcoma according to claim 3, wherein the body fluid is blood and the sample derived from the body fluid is plasma or is serum.

8. The method for detecting or diagnosing a rhabdomyosarcoma according to claim 1, wherein expression of at least one miRNA is normalized in each sample to hsa-miR-16 expression in that sample.

9. The method for detecting or diagnosing a rhabdomyosarcoma according to claim 2, wherein expression of at least one miRNA is normalized in each sample to hsa-miR-16 expression in that sample.

10. The method for detecting or diagnosing a rhabdomyosarcoma according to claim 3, wherein expression of at least one miRNA is normalized in each sample to hsa-miR-16 expression in that sample.

11. A method for detecting or diagnosing a rhabdomyosarcoma in a subject suspected of having a rhabdomyosarcoma comprising:
  quantifying expression of hsa-miR-206 in a first sample which is derived from a body fluid that is obtained from the subject suspected of having a rhabdomyosarcoma,
  quantifying expression of hsa-miR-206 in a second sample which is derived from a body fluid that is obtained from a normal subject; and
  comparing expression of hsa-miR-206 in the first sample with expression in the second sample,
  wherein detecting or diagnosing a rhabdomyosarcoma is obtained when there is increased expression of hsa-miR-206 in the first sample with respect to the second sample, and
  wherein expression is detected by real-time PCR and wherein the increased expression is evaluated is evaluated by having a P of less than 0.05 in a statistical test.

12. The method for detecting or diagnosing a rhabdomyosarcoma according to claim 11, wherein each of said steps of quantifying expression of hsa-miR-206 in a first and second sample comprises quantifying the expression of one or more additional miRNAs selected from the group consisting of hsa-miR-133a and hsa-miR-133b and wherein the one or more additional miRNAs have statistically significant increased expression by having a P of less than 0.05 in a statistical test.

13. The method for detecting or diagnosing a rhabdomyosarcoma according to claim 11, wherein the body fluid is blood and the sample derived from the body fluid is plasma or is serum.

14. The method for detecting or diagnosing a rhabdomyosarcoma according to claim 12, wherein the body fluid is blood and the sample derived from the body fluid is plasma or is serum.

15. The method for detecting or diagnosing a rhabdomyosarcoma according to claim 11, wherein expression of at least one miRNA is normalized in each sample to hsa-miR-16 expression in that sample.

16. The method for detecting or diagnosing a rhabdomyosarcoma according to claim 12, wherein expression of at least one miRNA is normalized in each sample to hsa-miR-16 expression in that sample.

* * * * *